United States Patent [19]

Nair et al.

[11] 4,393,055

[45] Jul. 12, 1983

[54] HYDROXYALKYL ETHER DERIVATIVES OF RUTIN POLY(H-)SULFATE AND METHOD OF USE

[75] Inventors: Vijay G. Nair, New York, N.Y.; Joseph P. Joseph, Montvale, N.J.; Seymour Bernstein, New City, N.Y.

[73] Assignee: American Cyanamid Company, Stamford, Conn.

[21] Appl. No.: 373,958

[22] Filed: May 3, 1982

[51] Int. Cl.$^3$ ...................... A61K 31/70; C07H 11/00
[52] U.S. Cl. ........................................ 424/180; 536/8; 536/18.1
[58] Field of Search .......................... 536/8, 122, 118; 424/180

[56] References Cited

U.S. PATENT DOCUMENTS

| | | | |
|---|---|---|---|
| 3,422,086 | 1/1969 | Carron et al. | 536/8 |
| 4,258,034 | 3/1981 | Joseph et al. | 536/122 |
| 4,258,180 | 3/1981 | Lewis et al. | 536/122 |
| 4,334,058 | 6/1982 | Nair et al. | 536/8 |
| 4,337,249 | 6/1982 | Conrow et al. | 536/122 |

*Primary Examiner*—Johnnie R. Brown
*Attorney, Agent, or Firm*—Barbara A. Shimei

[57] ABSTRACT

Hydroxyalkyl ether derivatives of rutin poly(H-)sulfate and salts thereof useful as complement inhibitors.

35 Claims, No Drawings

HYDROXYALKYL ETHER DERIVATIVES OF RUTIN POLY(H-)SULFATE AND METHOD OF USE

BACKGROUND OF THE INVENTION

1. Field of Invention

The present invention relates to novel hydroxyalkyl ether derivatives of rutin poly(H-)sulfates and salts thereof and their use as inhibitors of the complement system of warm-blooded animals.

2. Description of the Prior Art

Certain sulfated polysaccharides have been reported as having complement inhibiting activity, for example, heparin, J. Infect. Dis. 44: 250–253 (1929); carrageenin, Immunology 8: 291 (1965); and pentosan polysulfoester, Chemical Abstracts 75: 33179s (1971). The basic rutin poly(H-)sulfates and salts thereof are the subject of application Ser. No. 181,251, filed Aug. 25, 1980, now Pat. No. 4,334,058 and its parent applications Ser. No. 62,587, filed July 31, 1979, now abandoned, and Ser. No. 966,423, filed Dec. 4, 1978, now abandoned, all incorporated herein by reference. However, no art is known which discloses anticomplementary activity for the novel hydroxyalkyl derivatives of rutin poly(H-)sulfate which are the subject of this invention.

A rutin sulfate sodium salt ("rutin water soluble") is commercially available from E. Merck, Darmstadt, West Germany, Catalogue No. 500014. This material, which is useful as an injectable form of Vitamin P, has an analysis, $S=5.45\%$. "Rutin water soluble" has been tested for complement inhibiting activity, using the tests disclosed herein, and has been found lacking in complement inhibiting activity. Sulfation of "rutin water soluble" produces the rutin poly(H-)-sulfates of the aforementioned U.S. patent applications, (sulfur analysis $S=16.5\%$) which are active as complement inhibitors.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. World Health Org. 39: 935 (1968); Ann. Rev. Medicine 19: 1 (1968); The John Hopkins Med. J. 128: 57 (1971); Harvey Lectures 66: 75 (1972); The New England Journal of Medicine 287: 452, 489, 545, 592, 642 (1972); Scientific American 229(5): 54 (1973); Federation Proceedings 32: 134 (1973); Medical World News, October 11, 1974, p. 53; J. Allergy Clin. Immunol. 53: 298 (1974); Cold Spring Harbor Conf. Cell Proliferation 2/Proteases Biol. Control: 229 (1975); Ann. Review of Biochemistry 44: 697 (1975); Complement in Clinical Medicine, Disease-a-Month (1975); Complement, Scope, December 1975; Annals of Internal Medicine 84: 580 (1976); Transplant Reviews: 32 (1976); "Complement: Mechanisms and Functions", Prentice-Hall, Englewood Cliffs, N.J. (1976); Essays Med. Biochem. 2: 1 (1976); Hospital Practice 12: 33 (1977); Perturbation of Complement in Disease, Chap. 15 in Biological Amplification Systems in Immunology (Ed. Day and Good), Plenum, New York and London (1977); Am. J. Clin. Pathology 68: 647 (1977); Biochemical Soc. Transactions 5: 1659 (1977); The Harvey Lecture Series 72: 139 (1976-1977); J. Periodontology 48: 505 (1977); Biochemical Soc. Transactions 6: 798 (1978); Clin. and Experimental Dermatology 4: 271 (1979); Reviews of Infectious Diseases 1: 483 (1979).

The complement system (e.g. classical pathway) can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry 38: 389 (1969); J. Experimental Medicine 141: 724 (1975); J. of Immunology 116: 1431 (1976); 119: 1, 1195, 1358, 1482 (1977); 120: 1841 (1978); Immunochemistry 15: 813 (1978); J. Biological Chemistry 254: 9908 (1979).

A variety of substances have been disclosed as inhibiting the complement system i.e., as complement inhibitors. For example, the compounds, 3,3′-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry 12: 415, 902, 1049, 1053 (1969); Canadian Journal of Biochemistry 47: 547 (1969); The Journal of Immunology 104: 279 (1970); The Journal of Immunology 106: 241 (1971); The Journal of Immunology 111: 1061 (1973); Biochim. Biophys. Acta 317: 539 (1973); Life Sciences 13: 351 (1973); Journal of Immunology 113: 584 (1974); Immunology 26: 819 (1974); Journal of Medicinal Chemistry 17: 1160 (1974); Biochim. Biophys. Res. Comm 67: 225 (1975); Ann. N.Y. Acad. Sci. 256: 441 (1975); Journal of Medicinal Chemistry 19: 634, 1079 (1976); Journal of Immunology 118: 466 (1977); Arch. Int. Pharmacodyn. 226: 281 (1977); Biochem. Pharmacol. 26: 325 (1977); Journal Pharm. Sci. 66: 1367 (1977); Chem. Pharm. Bull. 25: 1202 (1977); Biochim. Biophys. Acta 484: 417 (1977); Journal Clin. Microbiology 5: 278 (1977); Immunochemistry 15: 231 (1978); Immunology 34: 509 (1978); J. Experimental Medicine 147: 409 (1978); Thrombosis Research 14: 179 (1979); J. Immunology 122: 2418 (1979); J. Chem. Soc. Chem. Comm. 726 (1979); Immunology 36: 131 (1979); Biochim. Biophys. Acta 611: 196 (1980); and J. Med Chem. 23:240 (1980).

It has been reported that the known complement inhibitors, epsilon-aminocaproic acid and tranexamic acid, have been used with success in the treatment of hereditary angioneurotic edema, a disease state resulting from an inherited deficiency of lack of function of the serum inhibitor of the activated first component of complement (C1 inhibitor), The New England Journal of Medicine 286: 808 (1972); 287: 452 (1972); Ann. Intern. Med 84: 580 (1976); J. Allergy and Clin. Immunology 60: 38 (1977). Also androgenic steroids have been used successfully in the treatment of this phisiological disorder; see Medicine 58: 321 (1979); Arthritis and Rheumatism 22: 1295 (1979); American J. Medicine 66: 681 (1979); and J. Allergy Clinical Immunology 65: 75 (1980).

It has also been reported that the drug pentosanpolysulfoester has an anticomplementary activity on human serum, both in vitro and in vivo, as judged by the reduction in total hemolytic complement activity; Pathologie Biologie 25: 33; 25 (2): 105; 25 (3): 179 (1977).

SUMMARY OF THE INVENTION

It has now been discovered that hydroxyalkyl ether derivatives of rutin poly(H-)sulfates interact with the complement reaction sequence, thereby inhibiting complement activity in body fluids.

This invention is particularly concerned with the pharmaceutically acceptable salts of hydroxyalkyl ether derivatives of rutin poly(H-)sulfate, having complement activity of the formula:

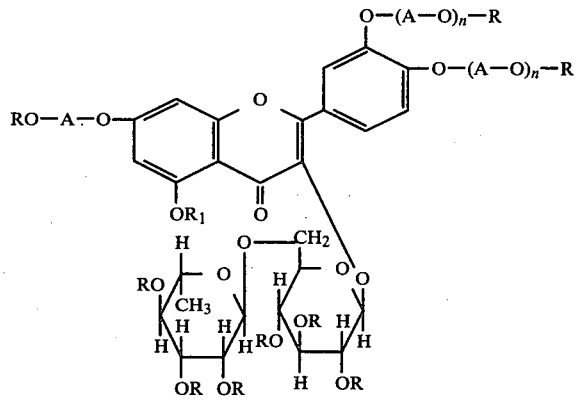

wherein A is $C_1$-$C_5$ alkyldiyl; n is an integer zero or one; R is $SO_3B$; $R_1$ is hydrogen or $SO_3B$; and B is a pharmaceutically acceptable salt cation, wherein the salt forming moiety is selected from the group alkali metal, alkaline earth metal, ammonia and substituted ammonia selected from the group $C_1$-$C_6$ trialkylamine, piperidine, pyrazine, $C_2$-$C_6$ alkanolamine, and $C_3$-$C_6$ cycloalkylamine.

This invention is also concerned with a method of inhibiting the complement system in a body fluid, such as blood serum, which comprises subjecting body fluid complement to the action of an effective complement inhibiting amount of a compound of the above formula. Body fluids can include blood, plasma, serum, synovial fluid, cerebrospinal fluid, or pathological accumulations of fluid such as pleural effusion, etc. This invention is further concerned with a method of inhibiting the complement system in a warm-blooded animal which comprises administering to said animal an effective complement inhibiting amount of a compound of the above formula.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as for example, inflammation following coronary occlusion. They may also be useful in the treatment of transplant rejection and ulcers and as blood culture and transport mediums.

DESCRIPTION OF THE PREFERRED EMBODIMENTS

The compounds of the present invention are those represented by the following generic formula:

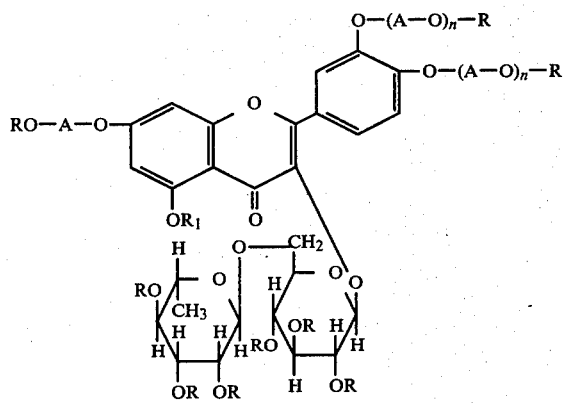

wherein A is $C_1$–$C_5$ alkyldiyl; n is an integer zero or one; R is $SO_3B$; $R_1$ is hydrogen or $SO_3B$; and B is a pharmaceutically acceptable salt cation, wherein the salt forming moiety is selected from the group alkali metal, alkaline earth metal, ammonia and substituted ammonia selected from the group $C_1$–$C_6$ trialkylamine, piperidine, pyrazine, $C_2$–$C_6$ alkanolamine and $C_3$–$C_6$ cycloalkylamine.

Preferably the moiety A is alkyldiyl of one to three carbon atoms, n is zero, $R_1$ is $SO_3B$ and B is an alkali metal salt cation.

Particularly preferred compounds of this invention which are of major interest are listed below, named as derivatives of rutin poly(H-)sulfate and by Chemical Abstracts nomenclature:

3′,4′,7-Tris(2-hydroxyethyl)rutin, deca(H-sulfate)-sodium salt
   3,5-Dihydroxy-3′,4′,7-tris(2-hydroxyethoxy)-3-(6-O-alpha-D-mannopyranosyl-beta-D-glucopyranoside), flavone, decakis(H-sulfate), decasodium salt 3′,4′,7-Tris(2-hydroxypropyl)rutin, deca(H-sulfate)-sodium salt
   3,5-Dihydroxy-3′,4′,7-tris(2-hydroxypropoxy)-3-[6-O-(6-deoxy-alpha-L-mannopyranosyl)-beta-D-glucopyranoside], flavone, decakis-(H-sulfate), decasodium salt 3′,4′,7-Tris(2-hydroxypropyl)rutin, nona(H-sulfate)-sodium salt
   3,5-Dihydroxy-3′,4′,7-tris(2-hydroxypropoxy)-3-[6-O-(6-deoxy-alpha-L-mannopyranosyl)-beta-D-glucopyranoside], flavone, 2″,2‴,3″,3‴,3⁗,4′,4″,4‴,7-nonakis(H-sulfate), nonasodium salt 7-(2-hydroxyethyl)rutin, deca(H-sulfate)sodium salt
   3,3′,4′,5-Tetrahydroxy-7-(2-hydroxyethoxy)-3-[6-O-(6-deoxy-alpha-L-mannopyranosyl)-beta-D-glucopyranoside], flavone, decakis(H-sulfate), decasodium salt 7-(2-hydroxyethyl)rutin, nona(H-sulfate)sodium salt
   3,3′,4′,5-Tetrahydroxy-7-(2-hydroxyethoxy)-3-[6-O-(6-deoxy-alpha-L-mannopyranosyl)-beta-D-glucopyranoside], flavone, 2″,2‴,3″,3‴,3⁗,4′4″,4‴,7-nonakis(H-sulfate), nonasodium salt 7-(2-hydroxypropyl)rutin, nona(H-sulfate)sodium salt
   3,3′,4′,5-tetrahydroxy-7-(2-hydroxypropoxy)-3-[6-O-6-deoxy-alpha-L-mannopyranosyl)-beta-D-glucopyranoside], flavone, 2″,2‴,3″,3‴,3⁗,4′,4″,4‴,7-nonakis(H-sulfate), nonasodium salt 7-(2-hydroxypropyl)rutin, deca(H-sulfate)sodium salt
   3,3′,4′,5-tetrahydroxy-7-(2-hydroxypropoxy)-3-[6-O-6-deoxy-alpha-L-mannopyranosyl)-beta-D-glucopyranoside], flavone, decakis(H-sulfate), decasodium salt The rutin poly(H-)sulfate salts which are the precursors of the compounds of this invention may be prepared by the application or adaption of known methods, for example, as described in Chemical Reviews 62: 549–589 (1962); and U.S. Pat. Nos. 3,271,388; 2,923,704; 2,686,779 and 2,697,093; or as described hereinbelow. These sulfate salts are solvated in varying degrees with water and ethanol. These known intermediates are then used in the preparation of the compounds of this invention.

The compounds of the present invention are prepared as described in Flowchart A.

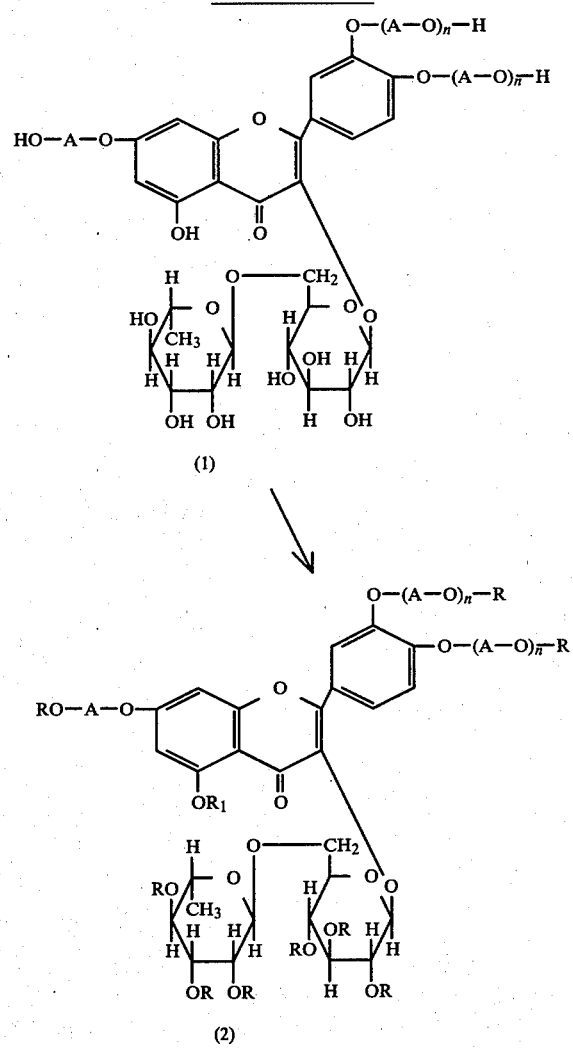

In accordance with Flowchart A, a hydroxyalkyl derivative of rutin (1), where A and n are as previously defined, is treated with a $C_1$–$C_6$ trialkylamine (preferably triethylamine)-sulfur trioxide composition in a solution or a solvent such as dimethylformamide or dimethylacetamide. The solution additionally may contain a drying agent such as calcium sulfate. Typically, the reaction proceeds at 20°–90° C. for 18–36 hours after which the rutin-trialkylammonium salt is separated. In a typical separation, the mixture is added to acetone and refrigerated, giving the hydroxyalkyl-rutin poly(H-sulfate)trialkylammonium derivative (2), where A and n are as previously defined, $R_1$ is hydrogen or $SO_3B$, R is $SO_3B$, and B is ($C_1$ to $C_6$ alkyl)$_3$NH. The trialkylammonium derivative (2) can be treated with an aqueous solution of a water soluble alkali or alkaline earth metal cation-containing compound (e.g., sodium acetate, potassium acetate, calcium acetate), or ammonia or a substituted ammonia selected from the group piperidine, pyrazine, $C_2$–$C_6$ alkanolamine, and $C_3$–$C_6$ cycloalkylamine, to give the hydroxyalkyl-rutin derivative of (2) wherein A, n, R, and $R_1$ are as described above and B is alkali metal, alkaline earth metal, ammonia, piperidine, pyrazine, $C_1$–$C_6$ alkanolamine, or $C_3$–$C_6$ cycloalkylamine.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Specific illustrations of typical separation and isolation procedures can be had by reference to the appropriate examples described hereinbelow; however, other equivalent separation procedures could, of course, also be used. Also, it should be appreciated that where typical reaction conditions (e.g. temperatures, mole ratios, reaction times) have been given above, that conditions both above and below these ranges can also be used, though generally less conveniently.

The term "$C_1$–$C_5$ alkyldiyl" refers to a divalent straight or branched chain fully saturated hydrocarbon having from 1 to 5 carbon atoms, e.g. methylene, ethylene, n-propylene, n-butylene, t-butylene, etc.

The term pharmaceutically acceptable salts refers to those salts of the parent compound which do not significantly adversely affect the pharmaceutical properties (e.g. toxicity, effectiveness, etc.) of the parent compound, such as are conventionally used in the pharmaceutical art. The salts of the present invention which are pharmaceutically acceptable cations include the alkali metals, e.g. sodium, potassium, etc.; alkaline earth metals, e.g. calcium etc.; ammonia; piperidine; pyrazine; $C_1$–$C_6$ trialkylamine; $C_2$–$C_6$ alkanolamine; and $C_3$–$C_6$ cycloalkylamine. The term "$C_1$–$C_6$ trialkylamine" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "$C_2$–$C_6$ alkanolamine" refers to the above defined trialkylamines additionally substituted with at least one and not more than three hydroxy groups on at least two of the alkyl hydrocarbon chains. Such amines are, for example, triethanolamine, tripropanolamine, etc. The term "$C_3$–$C_6$ cycloalkylamine" is defined as the 3 to 6 fully saturated carbocyclic moieties such as cyclopropyl, cyclobutyl, methylcyclobutyl, cyclopentyl, cyclohexyl, etc.

A further understanding of the invention can be had from the following non-limiting Preparations and Examples. As used hereinabove and below unless expressly stated to the contrary, all temperatures and temperature ranges refer to the centigrade system and the terms ambient or room temperature refer to about 20° C. The term percent or (%) refers to weight percent and the terms mole and moles refer to gram moles. The term equivalent refers to a quantity of reagent equal in moles to the moles of the preceding or succeeding reactant recited in the Preparation or Example in the terms of moles of finite weight or volume.

EXAMPLE 1

3′,4′,7-Tris(2-hydroxyethyl)rutin, deca(H-sulfate)sodium salt

A mixture of 370 mg. of 3′,4′,7-tris(2-hydroxyethyl)-rutin and 1.35 g. of triethylamine-sulfur trioxide in 10 ml. of dimethylacetamide containing 2.0 g. of calcium sulfate is heated at 60°–65° C. for 24 hours. The mixture is cooled to room temperature, poured into acetone and refrigerated for 48 hours. The solid is collected, giving 3′,4′,7-tris(2-hydroxyethyl)rutin, deca(H-sulfate)triethylamine salt.

The above triethylamine salt is converted to the desired sodium salt by treatment with aqueous sodium acetate, giving 300 mg. of the desired product.

EXAMPLE 2

3′,4′,7-Tris(2-hydroxypropyl)rutin, nona/deca(H-sulfate)sodium salt

A 25 g. portion of rutin is dissolved with stirring in 250 ml. of methanol, then 1.9 g. of sodium hydride (50% in oil) are added portionwise. The mixture is stirred ½ hour, a solution of 25 ml. of propylene oxide in 50 ml. of methanol is added, stirring is continued for one hour and then the mixture is refluxed for 72 hours. The mixture is cooled, adjusted to pH 4 with dilute hydrochloric acid, filtered and the filtrate is evaporated in vacuo to a gum. This gum is triturated with dichloromethane and dried. The resulting solid and gum are dissolved in 130 ml. of pyridine and 65 ml. of acetic anhydride are added. The mixture is allowed to stand overnight, then is poured into 1½ liters of ice-water giving a tan gum. The gum is isolated by decantation and washed twice with ice-water. The gum is dissolved in dichloromethane, dried over sodium sulfate, filtered through a pad of hydrous magnesium silicate and evaporated in vacuo to a gum. A 3.0 g. portion of this gum is impregnated on 10 g. of silica gel and added to a column of 400 g. of silica gel. The column is eluted with ethyl acetate:hexanes (1:1). Fractions with corresponding Rf values (as determined by thin-layer chromatography) are combined and evaporated to dryness, giving 1.28 g. of 3′,4′,7-tris(2-hydroxypropyl)rutin, decaacetate.

A 1.47 g. portion of 3′,4′,7-tris(2-hydroxypropyl)rutin, decaacetate (prepared as described above) is dissolved in 15 ml. of a solution of triethylamine:methanol:water (3:6:2). The solution is allowed to stand 18 hours, the solvents are evaporated, the residue is reevaporated twice from ether and then dried in vacuo for 18 hours. A 655 mg. portion of the resulting solid is redissolved in 11 ml. of the triethylamine:methanol:water solution and reprocessed as described above, giving 630 mg. of yellow solid. This solid is dissolved in methanol and a polystyrene sulfonic acid resin (e.g., Dowex 50(H+)®, Dow Chemical, Midland, Mich.) is added until the pH is acidic. The mixture is filtered and the filtrate evaporated, giving 615 mg. of 3',4',7-tris(2-hydroxypropyl)rutin.

A 400 mg. portion of 3',4',7-tris(2-hydroxypropyl)rutin is dissolved in 15 ml. of dimethylacetamide. A 2.0 g. portion of calcium sulfate and 1.38 g. of triethylamine sulfur trioxide are added and this mixture is stirred at 60°–65° C. for 18 hours. The mixture is cooled, filtered and the filtrate is poured into acetone. The solid is collected, giving 3',4',7-tris(2-hydroxypropyl)rutin, nona/-deca(H-sulfate)triethylamine salt which is converted to the sodium salt by the procedure described in Example 1, giving 395 mg. An analysis by high performance liquid chromatography shows the material to be approximately 48% 3',4',7-tris (2-hydroxypropyl)rutin nona(H-sulfate)sodium salt and 49% 3',4',7-tris(2-hydroxypropyl)rutin deca(H-sulfate) sodium salt.

EXAMPLE 3

7-(2-hydroxyethyl)rutin, deca(H-sulfate) sodium salt and nona(H-sulfate)-sodium salt A mixture of 1.962 g. of 7-monohydroxyethyl rutin (U.S. Pat. No. 4,153,788) and 16.2 g. of triethylamine sulfur trioxide in 40 ml. of dimethylacetamide containing 6.0 g. of calcium sulfate is heated at 60°–65° C. for 24 hours. The mixture is cooled to room temperature and divided into two equal portions A and B.

Portion A is combined with acetone and 5 ml. of triethylamine are added. The mixture is refrigerated giving a solid which is 7-(2-hydroxyethyl)rutin, deca(H-sulfate)triethylamine salt which is converted to the desired sodium salt as described in Example 1, giving 2.4 g. of colorless powder.

Portion B is combined with acetone and refrigerated giving 7-(2-hydroxyethyl)rutin, nona(H-sulfate)triethylamine salt which is then converted to the desired sodium salt as described in Example 1, giving 2.3 g. of pale yellow powder.

EXAMPLE 4

7-(2-hydroxypropyl)rutin, nona/deca(H-sulfate) sodium salt

A 10.1 g portion of sodium borate decahydrate is suspended in 55 ml. of distilled water in a pressure bottle and heated with stirring in an oil bath at 40° C. A 15.0 g portion of rutin is added and the mixture is stirred at 40° C. until solution is complete. An 8.7 ml. portion of propylene oxide is added and this reaction mixture is sealed and stirred at 40°–45° C. for 24 hours. The solution is cooled, opened, and concentrated in vacuo. The residual solution is adjusted to a pH of about 2 by addition of 6 N hydrochloric acid. Cooling overnight yields a solid precipitate which is removed by filtration and washed with distilled water at 0°–5° C. The filtrate is combined with the mother liquor and the mixture is adjusted to pH 7.0 and evaporated to dryness, then triturated with hot methanol and dried to give 3.8 g of an amorphous yellow solid. One gram of this amorphous yellow solid is dissolved in a mixture of 10 ml. of pyridine and 5 ml. of acetic anhydride and this reaction mixture is allowed to stand for 18 hours at room temperature (20°–25° C.). On pouring into ice water (0°–5° C.) a pale yellow solid is obtained which is purified by chromatography with ethyl acetate:hexane, 60:40 v/v on silica gel to yield a colorless glassy solid, 7-(2-hydroxypropyl)rutin, decaacetate.

A 0.17 g portion of sodium metal is added to 50 ml of methanol containing 7.0 g of 7-(2-hydroxypropyl)rutin decaacetate. The resulting deep orange solution is allowed to stand at room temperature (20°–25° C.) for 18 hours, during which time a yellow solid precipitates. The reaction mixture is concentrated in vacuo and the precipitate is collected by filtration to yield 2.6 g of 7-(2-hydroxypropyl)rutin.

A 2 g portion of calcium sulfate and 2.7 g of triethylamine-sulfur trioxide are added to 10 ml of dimethylacetamide containing 0.50 g of 7-(2-hydroxypropyl)rutin. This reaction mixture is stirred at 60°–70° C. for 18 hours, cooled, and filtered. The filtrate is poured into 200 ml of acetate and this mixture is allowed to stand overnight at 0°–5° C., yielding a gum which is separated by decanting the acetone supernatant. The gum is dissolved in a mixture of 5.0 ml of distilled water and 2.5 ml. of 30% aqueous sodium acetate and the resulting mixture is allowed to stand 15 minutes after which it is poured into 200 ml. of ethanol with rapid stirring, giving a finely divided yellow precipitate which by analysis by high performance liquid chromatography is a mixture of approximately 40% 7-(2-hydroxypropyl)rutin, deca(H-sulfate)sodium salt ($R_1 = SO_2ONa$) and 60% 7-(2-hydroxypropyl)rutin, nona(H-sulfate)sodium salt ($R_1 = $ hydrogen).

EXAMPLE 5

Preparation of Compressed Tablet

| Ingredient | mg./Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 6

Preparation of Compressed Tablet—Sustained Action

| Ingredient | mg./Tablet |
|---|---|
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 7

Preparation of Hard Shell Capsule

| Ingredient | mg./Capsule |
|---|---|
| Active Compound | 0.5–500 |
| Lactose, Spray Dried | qs |
| Magnesium Stearate | 1–10 |

EXAMPLE 8

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 9

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 10

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 11

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 12

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 13

Preparation of Intra-Articular Product

| Ingredient | Amount |
|---|---|
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 14

Preparation of Injectable Depo Suspension

| Ingredient | % W/V |
|---|---|
| Active Compound | 0.05–5 (acid equivalent) |
| Polysorbate 80 USP | 0.2 |
| Polyethylene glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 15

Preparation of Dental Paste

| Ingredient | % W/V |
|---|---|
| Active Compound | 0.05–5 |
| Zinc Oxide | 15 |
| Polyethylene Glycol 4000 USP | 50 |
| Distilled Water qs | 100 |

EXAMPLE 16

Preparation of Dental Ointment

| Ingredient | % W/V |
|---|---|
| Active Compound | 0.05–5 |
| Petrolatum, White USP qs | 100 |

EXAMPLE 17

Preparation of Dental Cream

| Ingredient | % W/V |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 18

Preparation of Topical Cream

| Ingredient | % W/V |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |

-continued

| Ingredient | % W/V |
| --- | --- |
| Purified Water qs | 100 |

EXAMPLE 19

Preparation of Topical Ointment

| Ingredient | % W/W |
| --- | --- |
| Active Compound | 0.05–5 |
| Cholesterol | 3 |
| Stearyl Alcohol | 3 |
| White Wax | 8 |
| Petrolatum, White USP qs | 100 |

EXAMPLE 20

Preparation of Spray Lotion (Non-aerosol)

| Ingredient | % W/V |
| --- | --- |
| Active Compound | 0.05–5 |
| Isopropyl Myristate | 20 |
| Alcohol (Denatured) qs | 100 |

EXAMPLE 21

Preparation of Buccal Tablet

| Ingredient | g./Tablet |
| --- | --- |
| Active Ingredient | 0.00325 |
| 6 x Sugar | 0.29060 |
| Acacia | 0.01453 |
| Soluble Starch | 0.01453 |
| F.D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 22

Preparation of Lozenge

| Ingredient | g./Lozenge |
| --- | --- |
| Active Ingredient | 0.0140 |
| Kompact ® Sugar (Sucrest Co.) | 0.7138 |
| 6 x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg./kg./day, or every six hours for more rapidly excreted salts, may be used. For intra-articular use for large joints such as the knee, from about 2 to about 20 mg./joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg./kg. to about 100 mg./kg. of body weight of animal per day. The usual daily dosage for a 70 kg. subject may vary from about 350 mg. to about 3.5 g. Unit doses of the acid or salt can contain from about 0.5 mg. to about 500 mg.

The compounds to the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Cap 50 Test—Here, appropriate amounts of the test compound are added to a pool of guinea pig serum in vitro, after which the undiluted serum capillary tube assay referred to above is run. The concentration of compound inhibiting 50% is reported; and (iii) Guinea Pig Intraperitoneal Test (GPIP)—Guinea pigs weighing about 300 g. are dosed intraperitoneally (i.p.) with 200 mg./kg. of the test compound dissolved in saline and adjusted to pH 7-8. Approximately 0.4 ml. blood samples, taken by orbital sinus puncture 30 minutes and one hour after injections, are collected directly into centrifuge tubes; 5 ml. blood samples, taken by decapitation 2 hours after injection are collected directly into beakers. The samples are allowed to clot, centrifuged, and the resultant sera are assayed for complement activity using the capillary complement assay. Percent inhibition are calculated by comparison with simultaneous controls.

The results appear in Table I, which shows that the principal compounds of the invention possess highly significant in vitro and in vivo complement inhibiting activity in warm-blooded animals.

TABLE I

| | Biological Activities | | | | |
|---|---|---|---|---|---|
| | | | In vivo Activity (Guinea Pig) Intraperitoneal % Inhibition | | |
| | In vitro Activity | | | | |
| | | Cap | Time (hours) | | |
| Compound | 026* | 50* | 4 | 6 | 24 |
| 3',4',7-Tris(2-hydroxyethyl)-rutin, deca(H—sulfate)sodium salt | 7–10** | 133 | 41 | 48 | −5 |
| | | 181 | 86 | 82 | 52 |
| 3',4',7-Tris(2-hydroxypropyl)-rutin, nona/deca(H—sulfate)-sodium salt | 10 | 122 | 84 | 74 | 29 |
| | | 92 | | | |
| 7-(2-hydroxyethyl)rutin, deca-(H—sulfate)sodium salt | 6–12 | 55 | 88 | 71 | 20 |
| 7-(2-hydroxyethyl)rutin, nona-(H—sulfate)sodium salt | 9–12 | 248 | 86 | 71 | 35 |
| | | 107 | | | |
| 7-(2-hydroxypropyl)rutin, nona/deca(H—sulfate)sodium salt | 9 | 142 | | | |

TABLE I-continued

| | Biological Activities | | | | |
|---|---|---|---|---|---|
| | | | In vivo Activity (Guinea Pig) Intraperitoneal % Inhibition | | |
| | In vitro Activity | | | | |
| | | Cap | Time (hours) | | |
| Compound | 026* | 50* | 4 | 6 | 24 |
| salt | | | | | |

*Code designation for tests employed as referred herein.
**Activity in wells, a serial dilution assay. Higher well number indicates higher activity. The serial dilutions are two-fold.

We claim:
1. A compound selected from those of the formula:

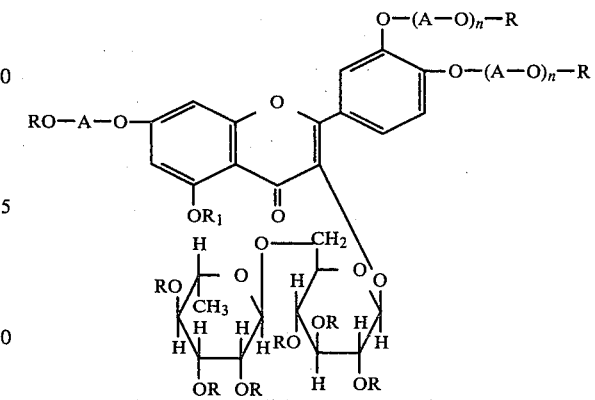

wherein A is $C_1$-$C_5$ alkyldiyl; n is an integer zero or one; R is $SO_3B$; $R_1$ is hydrogen or $SO_3B$; and B is a pharmaceutically acceptable salt cation, wherein the salt forming moiety is selected from the group alkali metal, alkaline earth metal, ammonia and substituted ammonia selected from the group $C_1$-$C_6$ trialkylamine, piperidine, pyrazine, $C_2$-$C_6$ alkanolamine and $C_3$-$C_6$ cycloalkylamine.

2. The compound according to claim 1, 3',4',7-tris(2-hydroxyethyl)rutin, deca(H-sulfate)sodium salt.

3. The compound according to claim 1, 3',4',7-tris(2-hydroxypropyl)rutin, deca(H-sulfate)sodium salt.

4. The compound according to claim 1, 3',4',7-tris(2-hydroxypropyl)rutin, nona(H-sulfate)sodium salt.

5. A composition of matter comprising a mixture of 3',4',7-tris(2-hydroxypropyl)rutin, nona(H-sulfate)-sodium salt and 3',4',7-tris(2-hydroxypropyl)rutin, deca(H-sulfate)sodium salt.

6. The compound according to claim 1, 7-(2-hydroxyethyl)rutin, deca(H-sulfate)sodium salt.

7. The compound according to claim 1, 7-(2-hydroxyethyl)rutin, nona(H-sulfate)sodium salt.

8. The compound according to claim 1, 7-(2-hydroxypropyl)rutin, nona(H-sulfate)sodium salt.

9. The compound according to claim 1, 7-(2-hydroxypropyl)rutin, deca(H-sulfate)sodium salt.

10. A composition of matter comprising a mixture of 7-(2-hydroxypropyl)rutin, nona(H-sulfate)sodium salt and 7-(2-hydroxypropyl)rutin, deca(H-sulfate)sodium salt.

11. A method of inhibiting the complement system in a body fluid which comprises subjecting said body fluid to the action of an effective complement inhibiting amount of a compound of the formula:

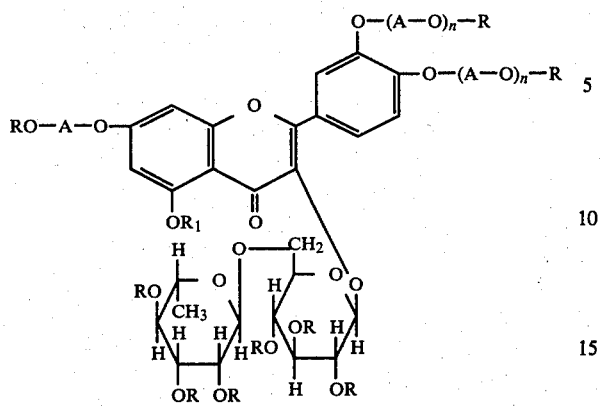

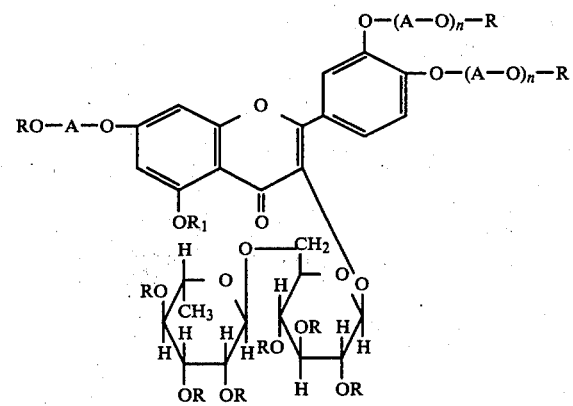

wherein A is $C_1$-$C_5$ alkyldiyl; n is an integer zero or one; R is $SO_3B$; $R_1$ is hydrogen or $SO_3B$; and B is a pharmaceutically acceptable salt cation, wherein the salt forming moiety is selected from the group alkali metal, alkaline earth metal, ammonia and substituted ammonia selected from the group $C_1$-$C_6$ trialkylamine, piperidine, pyrazine, $C_2$-$C_6$ alkanolamine and $C_3$-$C_6$ cycloalkylamine.

12. The method according to claim 11, wherein the compound is 3',4',7-tris(2-hydroxyethyl)rutin, deca(H-sulfate)sodium salt.

13. The method according to claim 11, wherein the compound is 3',4',7-tris(2-hydroxypropyl)rutin, deca(H-sulfate)sodium salt.

14. The method according to claim 11, wherein the compound is 3',4',7-tris(2-hydroxypropyl)rutin, nona(H-sulfate)sodium salt.

15. A method of inhibiting the complement system in a body fluid which comprises subjecting said body fluid to the action of an effective complement inhibiting amount of a composition of matter comprising a mixture of 3',4',7-tris(2-hydroxypropyl)rutin, nona(H-sulfate)sodium salt and 3',4',7-(2-hydroxypropyl)rutin, deca(H-sulfate)sodium salt.

16. The method according to claim 11, wherein the compound is 7-(2-hydroxyethyl)rutin, deca(H-sulfate)sodium salt.

17. The method according to claim 11, wherein the compound is 7-(2-hydroxyethyl)rutin, nona(H-sulfate)sodium salt.

18. The method according to claim 11, wherein the compound is 7-(2-hydroxypropyl)rutin, nona(H-sulfate)sodium salt.

19. The method according to claim 11, wherein the compound is 7-(2-hydroxypropyl)rutin, deca(H-sulfate)sodium salt.

20. A method of inhibiting the complement system in a body fluid which comprises subjecting said body fluid to the action of an effective complement inhibiting amount of a composition of matter comprising a mixture of 7-(2-hydroxypropyl)rutin, nona(H-sulfate)sodium salt and 7-(2-hydroxypropyl)rutin, deca(H-sulfate)sodium salt.

21. A method of inhibiting the complement system in a warm-blooded animal which comprises administering to said animal an effective complement inhibiting amount of a compound of the formula:

wherein A is $C_1$-$C_5$ alkyldiyl; n is an integer zero or one; R is $SO_3B$; $R_1$ is hydrogen or $SO_3B$; and B is a pharmaceutically acceptable salt cation, wherein the salt forming moiety is selected from the group alkali metal, alkaline earth metal, ammonia and substituted ammonia selected from the group $C_1$-$C_6$ trialkylamine, piperidine, pyrazine, $C_2$-$C_6$ alkanolamine and $C_3$-$C_6$ cycloalkylamine.

22. The method according to claim 21, wherein the compound is 3',4',7-tris(2-hydroxyethyl)rutin, deca(H-sulfate)sodium salt.

23. The method according to claim 21, wherein the compound is 3',4',7-tris(2-hydroxypropyl)rutin, deca(H-sulfate)sodium salt.

24. The method according to claim 21, wherein the compound is 3',4',7-tris(2-hydroxypropyl)rutin, nona(H-sulfate)sodium salt.

25. A method of inhibiting the complement system in a warm-blooded animal which comprises administering to said animal an effective complement inhibiting amount of a composition of matter comprising a mixture of 3',4',7-tris(2-hydroxypropyl)rutin, nona(H-sulfate)sodium salt and 3',4',7-tris(2-hydroxypropyl)rutin, deca(H-sulfate)sodium salt.

26. The method according to claim 21, wherein the compound is 7-(2-hydroxyethyl)rutin, deca(H-sulfate)sodium salt.

27. The method according to claim 21, wherein the compound is 7-(2-hydroxyethyl)rutin, nona(H-sulfate)sodium salt.

28. The method according to claim 21, wherein the compound is 7-(2-hydroxypropyl)rutin, nona(H-sulfate)sodium salt.

29. The method according to claim 21, wherein the compound is 7-(2-hydroxypropyl)rutin, deca(H-sulfate)sodium salt.

30. A method of inhibiting the complement system in a warm-blooded animal which comprises administering to said animal an effective complement inhibiting amount of a composition of matter comprising a mixture of 7-(2-hydroxypropyl)rutin, nona(H-sulfate)sodium salt and 7-(2-hydroxypropyl)rutin, deca(H-sulfate)sodium salt.

31. The method according to claim 21, 25, or 30, wherein the compound is administered internally.

32. The method according to claim 21, 25, or 30, wherein the compound is administered topically.

33. The method according to claim 21, 25, or 30, wherein the compound is administered periodontally in the oral cavity.

34. The method according to claim 21, 25, or 30, wherein the compound is administered intra-articularly.

35. The method according to claim 21, 25, or 30, wherein the compound is administered parenterally.

* * * * *